(12) United States Patent
Chaki et al.

(10) Patent No.: US 9,975,824 B2
(45) Date of Patent: May 22, 2018

(54) METHOD FOR PRODUCING 2,3,3,3-TETRAFLUOROPROPENE

(71) Applicant: DAIKIN INDUSTRIES, LTD., Osaka (JP)

(72) Inventors: Takehiro Chaki, Osaka (JP); Daisuke Karube, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 0 days. days.

(21) Appl. No.: 15/514,901

(22) PCT Filed: Jul. 7, 2015

(86) PCT No.: PCT/JP2015/069502
§ 371 (c)(1),
(2) Date: Mar. 28, 2017

(87) PCT Pub. No.: WO2016/051900
PCT Pub. Date: Apr. 7, 2016

(65) Prior Publication Data
US 2017/0233315 A1    Aug. 17, 2017

(30) Foreign Application Priority Data
Sep. 30, 2014 (JP) ................. 2014-200300

(51) Int. Cl.
C07C 17/20 (2006.01)
(52) U.S. Cl.
CPC .................. *C07C 17/206* (2013.01)
(58) Field of Classification Search
CPC ....... C07C 17/206; C07C 17/25; C07C 21/18; C07C 17/20; C07C 17/42; C07C 17/383; C07C 19/08
See application file for complete search history.

(56) References Cited

U.S. PATENT DOCUMENTS

| 2009/0240090 A1 | 9/2009 | Merkel |
| 2011/0130599 A1 | 6/2011 | Elsheikh et al. |
| 2013/0267740 A1 | 10/2013 | Wendlinger et al. |
| 2014/0031597 A1 | 1/2014 | Deur-Bert et al. |
| 2014/0121424 A1 | 5/2014 | Nose et al. |
| 2015/0080619 A1 | 3/2015 | Deur-Bert et al. |

FOREIGN PATENT DOCUMENTS

| JP | 2009-227675 | | 10/2009 |
| JP | 2011-525925 | | 9/2011 |
| JP | 2013-537167 | | 9/2013 |
| JP | 2014-500858 | | 1/2014 |
| JP | 2014-511349 | | 5/2014 |
| JP | 2014-523395 | | 9/2014 |
| WO | 2012/057367 | | 5/2012 |
| WO | 2012/099776 | | 7/2012 |
| WO | WO 2012/098420 | * | 7/2012 |
| WO | 2013/114015 | | 8/2013 |
| WO | WO 2013/114015 | * | 8/2013 |
| WO | 2014/025065 | | 2/2014 |
| WO | WO 2014/025065 | * | 2/2014 |

OTHER PUBLICATIONS

International Search Report dated Oct. 6, 2015 in International (PCT) Application No. PCT/JP2015/069502.
U.S. Appl. No. 61/511,663, filed Jul. 2011.
Extended European Search Report dated Mar. 28, 2018 in corresponding European Patent Application No. 15847924.6.

* cited by examiner

*Primary Examiner* — Jafar Parsa
(74) *Attorney, Agent, or Firm* — Wenderoth, Lind & Ponack, L.L.P.

(57) ABSTRACT

This invention provides a method capable of efficiently producing 2,3,3,3-tetrafluoropropene (HFO-1234yf) with a recycling step using substantially a single reaction step. A method for producing 2,3,3,3-tetrafluoropropene (HFO-1234yf), comprising a reaction step of reacting at least one chlorine-containing starting compound selected from the group consisting of chlorine-containing alkanes represented by formula (1): $CX_2YCHClCH_2Z$ (wherein X, Y and Z independently represent H, F or Cl) and chlorine-containing alkenes represented by formula (2): $CX_2YCCl=CZ_2$ (wherein X, Y and Z independently represent H, F or Cl) with a fluorinating agent, wherein the molar ratio of the chlorine-containing starting compound represented by formula (1) or (2) newly supplied to the reactor inlet is less than 1.2 relative to 2-chloro-3,3,3-trifluoropropene (HCFO-1233xf) in components obtained from the reactor outlet.

11 Claims, 1 Drawing Sheet

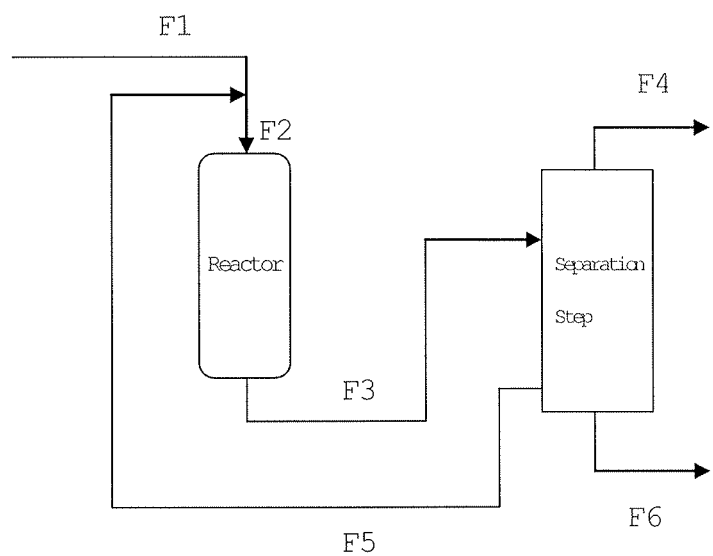

METHOD FOR PRODUCING 2,3,3,3-TETRAFLUOROPROPENE

TECHNICAL FIELD

The present invention relates to a method for producing 2,3,3,3-tetrafluoropropene.

BACKGROUND ART

Fluoroolefins represented by the formula: $CF_3(CX_2)_nCF=CH_2$, the formula: $CF_3(CX_2)_nCH=CHF$ (wherein X represents H or F, and n is an integer of 0 or more), and the like are useful compounds as various functional materials, solvents, refrigerants, blowing agents, and monomers for functional polymers or starting materials of such monomers. For example, fluoroolefins are used as monomers for modifying ethylene-tetrafluoroethylene copolymers. In particular, of the fluoroolefins mentioned above, 2,3,3,3-tetrafluoropropene (HFO-1234yf) represented by $CF_3CF=CH_2$ has recently gained attention because it offers promising prospects as a refrigerant compound of low global-warming potential.

A known method for producing HFO-1234yf is a method in which halopropane or halopropane used as a starting material is fluorinated with hydrogen fluoride (HF). For example, when 1,1,1,2,3-pentachloropropane (HCC-240db) used as a starting material is fluorinated in a gas phase, the reactions proceed in the route as described below (Patent Document 1).

$$CCl_3CHClCH_2Cl + 3HF \rightarrow CF_3CCl=CH_2 + 4HCl \quad (1)$$

$$CF_3CCl=CH_2 + HF \rightarrow CF_3CFClCH_3 \quad (2)$$

$$CF_3CFClCH_3 \rightarrow CF_3CF=CH_2 + HCl \quad (3)$$

Alternatively, the reactions may proceed in the route as described below without the reaction step of chemical reaction formula (2).

$$CCl_3CHClCH_2Cl + 3HF \rightarrow CF_3CCl=CH_2 + 4HCl \quad (1)$$

$$CF_3CCl=CH_2 + HF \rightarrow CF_3CF=CH_2 + HCl \quad (4)$$

(Patent Document 2)

Further, as another method for producing HFO-1234yf, it is also possible to produce HFO-1234yf in a manner similar to the method represented by chemical reaction formulas (1) to (3) using 1,1,2,3-tetrachloropropene (HCO-1230xa) as a starting material instead of HCC-240db (Patent Document 3).

In all of the above methods that have previously been suggested, 2, 3, or more reaction steps are required to produce the desired HFO-1234yf from the starting material, i.e., halopropane or halopropene. In contrast, Patent Documents 4 and 5 found a method of producing HFO-1234yf by fluorinating the starting material, i.e., halopropane or halopropene, in a single reactor, although the yield is small. Patent Documents 4 and 5 also suggest a process for recycling 2-chloro-3,3,3-trifluoropropene (HCFO-1233xf), which is the major product of the reaction and may be used as an intermediate of HFO-1234yf. However, when the recycling process is actually performed with the conditions specified in the Examples of these prior art documents, unreacted HCFO-1233xf, HF, and the like successively increase in the system, making it impossible to constantly carry out the step. Therefore, to solve this problem, a step of removing unreacted HCFO-1233xf, HF, and the like to the outside of the system, a storing device, a separate reaction treatment, and the like will be necessary, thereby increasing facility cost and production cost.

CITATION LIST

Patent Documents

Patent Document 1: JP2009-227675A
Patent Document 2: JP2013-537167A
Patent Document 3: WO2012/099776A
Patent Document 4: U.S. 61/511,663A
Patent Document 5: JP2014-511349A

SUMMARY OF INVENTION

Technical Problem

The present invention has been accomplished in light of the circumstances of the prior art described above, and its major object is to provide a method of producing 2,3,3,3-tetrafluoropropene (HFO-1234yf) using, as a starting material, at least one chlorine-containing compound selected from the group consisting of chlorine-containing alkanes represented by formula (1):

$$CX_2YCHClCH_2Z$$

(wherein X, Y and Z independently represent H, F or Cl); and chlorine-containing alkenes represented by formula (2):

$$CX_2YCCl=CZ_2$$

(wherein X, Y and Z independently represent H, F or Cl), wherein the recycling process is established by a substantially single reaction step. With such a method, the present invention reduces energy costs and equipment costs, and efficiently produces HFO-1234yf in an economically advantageous manner.

Solution to Problem

The present inventors conducted extensive research to achieve the above object. As a result, the present inventors found that, in the method of producing 2,3,3,3-tetrafluoropropene (HFO-1234yf) using the above-specified chlorine-containing compound as a starting material, by performing a recycling process with substantially a single reaction step and required separation step, purification step, and the like by controlling the ratio of the starting material, i.e., the chlorine-containing compound, to the fluorinating agent, instead of a previously known production method with substantially two or more reaction steps, it is possible to reduce equipment costs, as well as energy costs required for heating and cooling, compared with the previously known method. The present invention was completed by further research based on the above findings.

Specifically, the present invention provides methods for producing HFO-1234yf detailed below.
Item 1.
A method for producing 2,3,3,3-tetrafluoropropene (HFO-1234yf), comprising the step of reacting at least one chlorine-containing starting compound selected from the group consisting of:
  chlorine-containing alkanes represented by formula (1):

$$CX_2YCHClCH_2Z$$

(wherein X, Y and Z independently represent H, F or Cl); and
  chlorine-containing alkenes represented by formula (2):

$$CX_2YCCl=CZ_2$$

(wherein X, Y and Z independently represent H, F or Cl) with a fluorinating agent, wherein the molar ratio of the chlorine-containing starting compound newly supplied to a reactor inlet is less than 1.2 relative to the molar amount of 2-chloro-3,3,3-trifluoropropene (HCFO-1233xf) in components obtained from a reactor outlet.

Item 2.

The method according to Item 1, wherein the molar ratio of the fluorinating agent supplied to the reactor is more than 50 relative to the molar amount of the chlorine-containing starting compound newly supplied to the reactor inlet.

Item 3.

The method according to Item 1 or 2, wherein the pressure in the reaction step is 0 to 0.3 MPaG.

Item 4.

The method according to any one of Items 1 to 3, wherein the molar ratio of the chlorine-containing starting compound newly supplied to the reactor inlet is 0.3 or less relative to the molar amount of HCFO-1233xf in the components obtained from the reactor outlet.

Item 5.

The method according to any one of Items 1 to 4, further comprising circulating at least a part of a product of the reaction step, and unreacted chlorine-containing starting compound and fluorinating agent in the reactor outlet to the reaction step.

Item 6.

The method according to any one of Items 1 to 5, further comprising separating HFO-1234yf and/or HCl from a product of the reaction step obtained in the reactor outlet, and circulating at least a part of a remaining product, and unreacted chlorine-containing starting compound and fluorinating agent to the reaction step.

Item 7.

The method according to any one of Items 1 to 6, wherein at least one chlorine-containing starting compound of the compounds represented by formula (1) is 1,1,1,2,3-pentachloropropane (HCC-240db).

Item 8.

The method according to any one of Items 1 to 6, wherein at least one chlorine-containing starting compound of the compounds represented by formula (2) is 1,1,2,3-tetrachloropropene (HCO-1230xa).

Item 9.

The method according to any one of Items 1 to 8, wherein the concentration of HCl contained in the components obtained from the reactor outlet in the reaction step is 10 mol % or less relative to the total amount of the components obtained from the reactor outlet.

Item 10.

The method according to any one of Items 1 to 9, wherein the fluorinating agent is anhydrous hydrogen fluoride.

Item 11.

The method according to any one of Items 1 to 10, wherein a catalyst used in the reaction step is a chromium oxide or a fluorinated chromium oxide.

Item 12.

The method according to any one of Items 1 to 11, wherein the concentration of HCl contained in components that are circulated to the reaction step is 5 mol % or less relative to a chlorine-containing compound to be circulated.

Item 13.

The method according to any one of Items 1 to 12, wherein $O_2$ and/or $Cl_2$ is introduced in the reaction step.

Advantageous Effects of Invention

With the method of the present invention, 2,3,3,3-tetrafluoropropene (HFO-1234yf) can be efficiently produced from at least one chlorine-containing starting compound selected from the group consisting of chlorine-containing alkanes represented by formula (1):

$$CX_2YCHClCH_2Z$$

(wherein X, Y and Z independently represent H, F or Cl); and chlorine-containing alkenes represented by formula (2):

$$CX_2YCCl=CZ_2$$

(wherein X, Y and Z independently represent H, F or Cl) with reduced energy costs and equipment costs in an economically advantageous manner.

BRIEF DESCRIPTION OF DRAWINGS

FIG. 1 is a flow chart showing the reaction steps in Examples 1 and 2, and Comparative Examples 1 to 3.

The separation step in the FIGURE designates the entire separation process including the various separation methods described above. The conditions of the separation step may be suitably selected.

DESCRIPTION OF EMBODIMENTS

The present invention is described in detail below. The various propanes and propenes relating to the present invention are defined in Table 1. However, in some of the tables, the characters before the number are omitted.

TABLE 1

| Code | Chemical Name | Chemical Formula |
| --- | --- | --- |
| HFO-1234yf | 2,3,3,3-tetrafluoropropene | $CF_3CF=CH_2$ |
| HCC-240db | 1,1,1,2,3-pentachloropropane | $CCl_3CHClCH_2Cl$ |
| HCO-1230xa | 1,1,2,3-tetrachloropropene | $CH_2ClCCl=CCl_2$ |
| HCFO-1233xf | 2-chloro-3,3,3-trifluoropropene | $CF_3CCl=CH_2$ |

In the present invention, HFO-1234yf may be obtained through substantially a single reaction step from at least one chlorine-containing starting compound selected from the group consisting of chlorine-containing alkanes represented by formula (1):

$$CX_2YCHClCH_2Z$$

(wherein X, Y and Z independently represent H, F or Cl) and chlorine-containing alkenes represented by formula (2):

$$CX_2YCClCZ_2$$

(wherein X, Y and Z independently represent H, F or Cl).

The production method of the present invention comprises: a reaction step of reacting a specific chlorine-containing starting compound with a fluorinating agent to generate HFO-1234yf; a step of separating the desired HFO-1234yf from unreacted chlorine-containing starting compound, fluorinating agent, intermediates, and by-products such as HCl in the components obtained from the reactor outlet; a step of purifying the HFO-1234yf separated in the separation step; and a step of recycling at least a part of the unreacted chlorine-containing starting compound, fluorinating agent and intermediates separated in the separation step so as to reuse it in the above reaction step.

This method is merely an embodiment of the production method of the present invention, and the production method of the present invention may further comprise, for example, a separation and purification step for the fluorinating agent, chlorine-containing fluoride that may be used as an intermediate of HFO-1234yf, a by-product such as HCl, and the like from the components in the respective steps. Further, the production method of the present invention may also comprise a removal step of removing the fluorinating agent, HF, HCl and the like from the components in the respective steps. The essential feature of the present invention is production of HFO-1234yf using substantially a single reaction step. The "substantially a single reaction step" herein means a step under a condition with identical reaction pressure and identical reaction temperature. The conditions are regarded as being substantially identical insofar as the differences in pressure and temperature are within a range of operational variation that occurs during the step, such as differences within a range of about ±10-20% in absolute pressure and absolute temperature.

In the embodiments of the present invention, the HCl concentration in the components to be recycled and reused is preferably 5 mol % or less, more preferably 1 mol % or less, relative to the chlorine-containing compound to be recycled and reused.

When circulation is performed, generally, a chlorine-containing starting compound and a fluorinating agent are newly supplied to the reactor; however, when the recycling process is actually performed by a previously-suggested method (the method with the conditions specified in the Examples of Patent Document 4, Patent Document 5, etc.), unreacted HCFO-1233xf, HF, and the like successively increase in the reaction system, making it impossible to constantly carry out the process.

In contrast, as a result of extensive research by the present inventors, it was found that when the recycling process was performed under the conditions of the present invention, a constant operation was possible by newly supplying a chlorine-containing starting compound in substantially the same amount as that of the generated HFO-1234yf, and/or a fluorinating agent in substantially the same amount as that of the generated HCl.

The method of the present invention having these features makes it possible to efficiently obtain HFO-1234yf with reduced energy and equipment costs in an economically advantageous manner.

The steps of the present invention are specifically explained below.

(1) Reaction Step

At least one chlorine-containing starting compound selected from the group consisting of chlorine-containing alkanes represented by formula (1):

(wherein X, Y and Z independently represent H, F or Cl) and chlorine-containing alkenes represented by formula (2):

(wherein X, Y and Z independently represent H, F or Cl) is used as a starting material and is reacted with a fluorinating agent in the presence or absence of a catalyst, thereby performing a fluorination reaction. As a result, HFO-1234yf is obtained.

Examples of usable fluorinating agents include anhydrous hydrogen fluoride, fluorine, trifluoromethane, and the like. In particular, anhydrous hydrogen fluoride is preferred.

The at least one chlorine-containing compound selected from the group consisting of chlorine-containing alkanes represented by formula (1) and chlorine-containing alkenes represented by formula (2), which is used as a starting material, is a known compound that can be easily obtained.

A method in which fluorination is performed by conducting a reaction using anhydrous hydrogen fluoride in a gas phase in the presence of a fluorination catalyst is specifically explained below as a reaction example.

Examples of usable fluorination catalysts include known catalysts that are active in a fluorination reaction with hydrogen fluoride. In particular, it is preferable to use a chromium-atom-containing fluorination catalyst. By using such a catalyst and reacting the chlorine-containing compound and anhydrous hydrogen fluoride as starting materials according to the conditions described below, it is possible to obtain HFO-1234yf.

Examples of usable chromium-atom-containing fluorination catalysts include chromium halides, chromium oxides, and the like. Of these, examples of preferred catalysts include $CrCl_3$, $CrF_3$, $Cr_2O_3$, $CrO_2$, $CrO_3$, and the like. These catalysts may be supported on a carrier. There is no particular limitation on the carrier, and examples of carriers include porous alumina silicates typified by zeolite, aluminum oxide, silicon oxide, activated carbon, titanium oxide, zirconium oxide, zinc oxide, aluminum fluoride, and the like.

In the present invention, it is particularly preferable to use at least one catalyst selected from the group consisting of chromium oxide and fluorinated chromium oxide.

Among these catalysts, the chromium oxide, for instance, is not particularly limited. For example, it is preferable to use chromium oxide represented by the composition formula: $CrO_m$, wherein m falls within the range of preferably $1<m<3$, more preferably $1<m<2$. Any chromium oxide catalysts in the form of powder, pellets, or the like may be used, as long as they are suitable for the reaction. Fluorinated chromium oxides may be prepared, for example, by fluorinating the above chromium oxides with hydrogen fluoride (HF treatment).

Further, chromium-based catalysts comprising, as a main component, a chromium compound containing at least one metallic element selected from the group consisting of indium, gallium, cobalt, nickel, zinc, aluminum, vanadium, and niobium may also be used as the chromium oxide catalyst or fluorinated chromium oxide catalyst. Further, the chromium-based catalyst may be any of amorphous chromium-based catalysts, and partly crystalline or entirely crystalline chromium-based catalysts.

When the fluorination reaction is performed using anhydrous hydrogen fluoride as a fluorinating agent, the anhydrous hydrogen fluoride may be generally supplied to the reactor together with the chlorine-containing compound used as a starting material. To achieve a high yield of the desired HFO-1234yf, the amount of anhydrous hydrogen fluoride to be supplied to the reactor is preferably about 10 mol or more, more preferably more than 50 mol, and further preferably about 100 mol or more, per mol of the chlorine-containing compound newly supplied to the reactor as a starting material. The amount of the anhydrous hydrogen fluoride preferably falls within the above range in terms of the selectivity of HFC-1234yf, retaining catalytic activity, productivity, and the like. Generally, the amount of anhydrous hydrogen fluoride is preferably about 500 mol or less, and more preferably about 400 mol or less, per mol of the chlorine-containing compound newly supplied to the reactor as a starting material. Further, the concentration of HCl contained in the components obtained from the reactor outlet is preferably 10 mol % or less based on the total amount of the components obtained from the reactor outlet.

Although the concentration of the anhydrous hydrogen fluoride to be supplied to the reactor is set in the above range, in order to successively produce HFO-1234yf in a substantially single reaction step, i.e., in order to keep the balance between the amount of newly supplied chlorine-containing starting compound and the production amount of HFO-1234yf, it is necessary to adjust the amount of the anhydrous hydrogen fluoride to be supplied, as well as various reaction conditions including the reaction temperature, the reaction pressure, and the contact time. The optimum amount of anhydrous hydrogen fluoride in the present reaction generally cannot be easily found since it greatly influences the amount of HCl produced as a by-product. The inventors of the present invention found the optimum condition range by conducting extensive research.

A method in which a fluorination catalyst is placed into a tubular flow reactor, and the chlorine-containing compound and anhydrous hydrogen fluoride used as starting materials are introduced into the reactor can be given as one specific embodiment of the method of the present invention.

The lower limit of the reaction temperature is not particularly limited because a lower reaction temperature is advantageous in terms of reducing decomposition of the starting materials and the products. The reaction temperature is preferably 300° C. or more, and more preferably 350° C. or more.

The reaction temperature is preferably about 500° C. or less in terms of retaining catalytic activity, suppressing the production of isomers as by-products, and the like. The reaction temperature is further preferably about 350 to 450° C.

The pressure during the reaction is not particularly limited, and the reaction may be performed under reduced pressure, ordinary pressure, or increased pressure. Although the reaction may be generally carried out at a pressure near atmospheric pressure (0.1 MPaG), it can also proceed smoothly under reduced pressure of less than 0.1 MPaG. Further, the reaction may be performed under increased pressure within a range in which the starting materials do not liquefy. However, in terms of suppressing a decrease in selectivity of the desired HFO-1234yf, suppressing a decrease in the duration of life of the catalyst, and the like, the pressure upon the reaction is preferably 1 MPaG or less, more preferably 0.7 MPaG or less, and further preferably 0.3 MPaG or less.

There is no limitation on the contact time. For example, the contact time, which is represented by $W/F_0$, is preferably about 0.5 to 50 g·sec/mL, and more preferably about 1 to 30 g·sec/mL. $W/F_0$ is the ratio of the catalyst amount W(g) to the total flow rate $F_0$ (flow rate at 0° C., 0.1013 MPa: cc/sec) of the starting material gases supplied to the reaction system.

The starting materials may be supplied to the reactor as is, or a gas that is inert to the starting materials and catalyst, such as nitrogen, helium, or argon, may be present together with the starting materials. The concentration of the inert gas is about 0 to 80 mol % based on the amount of gaseous components introduced into the reactor.

Further, when the reaction is performed in a gas phase in the presence of a catalyst, $O_2$ and/or $Cl_2$ may be supplied to the reaction apparatus together with the starting materials to maintain catalytic activity for a long period of time. This suppresses a decrease in catalytic activity.

(2) Separation Step

In the present invention, the HFO-1234yf produced in the above reaction step is separated from unreacted chlorine-containing starting compound, fluorinating agent, intermediates, and by-products such as HCl, and at least a part of the unreacted chlorine-containing starting compound, fluorinating agent and intermediates is recycled and reused in the above reaction step. This separation step may be performed in an arbitrary manner, and may include multiple different separation methods. More specifically, the separation step may be distillation, liquid-liquid separation, extractive distillation, liquid-liquid extractive separation, or a combination of these steps. These steps are merely examples, and do not limit the separation step to carry out the present invention. Any separation step and conditions may be used insofar as the HFO-1234yf-containing fraction can be separated from a fraction substantially free of HFO-1234yf so that the fraction substantially free of HFO-1234yf is recycled and reused in the reaction step. In this case, in order to ensure that the components to be recycled and reused are substantially free of HFO-1234yf, the HFO-1234yf-containing fraction preferably contains HFO-1234yf in the substantially same amount as that of the HFO-1234yf introduced in the separation step. Further, as described above, HCl during the reaction decreases the yield of the desired HFO-1234yf, and, in some cases, even causes an increase of unnecessary by-products that cannot be used as intermediates of the desired HFO-1234yf. Therefore, the HCl concentration in the components to be recycled from the separation step and reused in the reaction step is preferably as low as possible. The HCl concentration is preferably 5 mol % or less, and more preferably 1 mol % or less, relative to the chlorine-containing starting compound in the components to be recycled and reused. Thus, the HFO-1234yf-containing fraction may contain HCl, and it is possible to finally obtain a HFO-1234yf fraction substantially free of HCl in the HFO-1234yf purification step.

If necessary, the component free of HFO-1234yf separated in this separation step may be further subjected to a crude purification treatment step (separation step), such as distillation, to separate at least one member selected from the group consisting of unreacted chlorine-containing starting compound, intermediates, and fluorinating agent individually usable in the reaction step from a chlorine-containing fluorine compound that cannot be used as an intermediate of HFO-1234yf. Thereafter, at least a part of the unreacted chlorine-containing starting compound, fluorinating agent and intermediates individually usable in the reaction step may be recycled and reused in the reaction step.

It is possible to separate unreacted chlorine-containing starting compound, fluorinating agent, intermediates, and the like usable in the reaction step also from the HFO-1234yf-containing fraction after the HFO-1234yf fraction is further subjected to a HFO-1234yf purification step, and to recycle and reuse it in the reaction step.

Examples of intermediates as used herein include compounds produced as a result of reactions such as replacement of chlorine atom(s) by fluorine, hydrogen fluoride addition, dehydrochlorination, or dehydrofluorination of the chlorine-containing compound used as a starting material. Although it depends on the steps and the reaction conditions thereof, specific examples of intermediates include 1,1,2,3-tetrachloro-1-fluoropropane (HCFC-241db), 1,1,2-trichloro-1,3-difluoropropane (HCFC-242dc), 2,3,3-trichloro-3-fluoropropene (HCFO-1231xf), 2,3-dichloro-3,3-difluoropropene (HCFO-1232xf), 2-chloro-3,3,3-trifluoropropene (HCFO-1233xf), 1,1,1,2,2-pentafluoropropane (HFC-245cb), and the like.

When a fraction obtained in the separation step is recycled and reused, an acid removal step, a moisture removal step, a crude purification step such as distillation, and the like may be performed if necessary. The conditions in these steps may be appropriately set depending on the components to be separated.

When distillation is adopted in the separation step, the following is a specific example of the conditions when hydrogen fluoride (HF) is used as the fluorinating agent in the reaction step.

The conditions in the separation of the components that are obtained from the reactor outlet in the reaction step and to be recycled and reused in the reaction step from HFO-1234yf may be conditions in the separation of unreacted chlorine-containing starting compound, HF, intermediates, and the like as high-boiling-point components, and HFO-1234yf, hydrogen chloride and the like as low-boiling-point components. Since the chlorine-containing starting compound and the intermediates in the present invention have boiling points higher than that of the desired HFO-1234yf, the high-boiling-point components thus separated may be recycled and reused in the reaction step. The components that cannot be used as intermediates of HFO-1234yf contained in the high-boiling-point components may be separated from the components to be recycled by being subjected to a separation step before the components are circulated to the reaction step. Further, also to suppress degradation of the catalyst used in the reaction step, it is preferable to separate and remove the components that cannot be used as intermediates of HFO-1234yf from the components to be recycled and reused.

The components containing HFO-1234yf and hydrogen chloride and the like separated as low-boiling-point components can further be subjected to any purification step, such as single- or multi-stage distillation, liquid separation, extraction, or extractive distillation, to separate and collect HFO-1234yf from the components containing HFO-1234yf and hydrogen chloride and the like separated as low-boiling-point components. For example, when a distillation operation is performed as a separation means, the components containing HFO-1234yf and hydrogen chloride and the like separated as low-boiling-point components are subjected to a single- or multi-stage distillation step, thereby collecting high-purity HFO-1234yf from the bottom or a middle portion of the final distillation column. Hydrogen chloride can be collected from the top of the distillation column and reused for the desired purpose. Other organic components contained in the hydrogen chloride-containing fraction are chlorine-containing fluorides, which can be used as intermediates in the fluorination reaction step. Thus, these organic components can be separated from other components in the step of collecting HFO-1234yf, and can be recycled and reused in the reaction step. Further, when $O_2$ is introduced in the fluorination reaction step so as to retain the duration of life of the catalyst, the hydrogen chloride-containing fraction contains $O_2$, which may be recycled and reused in the reaction step.

EXAMPLES

The present invention is described in more detail below with reference to Examples. However, the present invention is not limited to the Examples.

Example 1

A fluorination reaction was performed in accordance with the flow chart shown in FIG. 1 with substantially a single reactor using HCC-240db as a starting material, thereby producing HFO-1234yf.

A Hastelloy reactor was used as a reactor, and 21 g of chromium oxide containing $Cr_2O_3$ as a main component (obtained by baking chromium hydroxide in the air under atmospheric pressure at 700° C. or more for two hours or more) was placed in the reactor as a catalyst. As a pretreatment before the use of the catalyst for the reaction, anhydrous hydrogen fluoride diluted with nitrogen was passed through, and the temperature of the reactor was raised from 200° C. to 360° C., and a fluorination treatment was performed.

The reactor was heated with an electric furnace. After the temperature reached a predetermined level, an operation of the reaction step shown in FIG. 1 was started. $O_2$ was introduced from the reactor inlet in an amount of 10 mol % relative to all of the organic substances in the reactor inlet.

The operating conditions of the reaction were as follows: the pressure was 0.0 MPaG and the temperature was 365° C. The formulations of the components at each stage (F1 to F6 in FIG. 1) of the reaction step were analyzed using gas chromatography. Table 2 below shows the analysis results.

TABLE 2

| Stage of the Step | F1 | F2 | F3 | F4 | F5 | F6 |
|---|---|---|---|---|---|---|
| HF (mol/min) | $0.20 \times 10^{-3}$ | $4.91 \times 10^{-3}$ | $4.71 \times 10^{-3}$ | 0 | $4.71 \times 10^{-3}$ | 0 |
| 240db (mol/min) | $5.43 \times 10^{-5}$ | $5.43 \times 10^{-5}$ | 0 | 0 | 0 | 0 |
| 1234yf (mol/min) | 0 | 0 | $4.73 \times 10^{-5}$ | $4.73 \times 10^{-5}$ | 0 | 0 |
| 1233xf (mol/min) | 0 | $4.24 \times 10^{-4}$ | $4.24 \times 10^{-4}$ | 0 | $4.24 \times 10^{-4}$ | 0 |
| 245cb (mol/min) | 0 | $1.25 \times 10^{-5}$ | $1.25 \times 10^{-5}$ | 0 | $1.25 \times 10^{-5}$ | 0 |
| 1223xd (mol/min) | 0 | 0 | $4.68 \times 10^{-7}$ | 0 | 0 | $4.68 \times 10^{-7}$ |
| 1233zd (mol/min) | 0 | 0 | $4.68 \times 10^{-7}$ | 0 | 0 | $4.68 \times 10^{-7}$ |
| 1234ze (mol/min) | 0 | 0 | $4.68 \times 10^{-7}$ | 0 | 0 | $4.68 \times 10^{-7}$ |
| 245fa (mol/min) | 0 | 0 | 0 | 0 | 0 | 0 |
| 1243zf (mol/min) | 0 | 0 | $4.68 \times 10^{-7}$ | 0 | 0 | $4.68 \times 10^{-7}$ |
| Others (mol/min) | 0 | 0 | $5.05 \times 10^{-6}$ | 0 | 0 | $5.05 \times 10^{-6}$ |
| HCl (mol/min) | 0 | 0 | $2.71 \times 10^{-4}$ | $2.71 \times 10^{-4}$ | 0 | 0 |

Example 2

A fluorination reaction was performed in accordance with the flow chart shown in FIG. 1 with substantially a single reactor using HCC-240db as a starting material, thereby producing HFO-1234yf.

A Hastelloy reactor was used as a reactor, and 15 g of chromium oxide containing $Cr_2O_3$ as a main component (obtained by baking chromium hydroxide in the air under atmospheric pressure at 700° C. or more for two hours or more) was placed in the reactor as a catalyst. As a pretreatment before the use of the catalyst for the reaction, anhydrous hydrogen fluoride diluted with nitrogen was passed through, and the temperature of the reactor was raised from 200° C. to 380° C., and a fluorination treatment was performed.

The reactor was heated with an electric furnace. After the temperature reached a predetermined level, an operation of the reaction step shown in FIG. 1 was started. $O_2$ was introduced from the reactor inlet in an amount of 10 mol % relative to all of the organic substances in the reactor inlet.

The operating conditions of the reaction were as follows: the pressure was 0.12 MPaG and the temperature was 380° C. The formulations of the components at each stage (F1 to F6 in FIG. 1) of the reaction step were analyzed using gas chromatography. Table 3 below shows the analysis results.

TABLE 3

| Stage of the Step | F1 | F2 | F3 | F4 | F5 | F6 |
|---|---|---|---|---|---|---|
| HF (mol/min) | $0.21 \times 10^{-3}$ | $2.54 \times 10^{-3}$ | $2.33 \times 10^{-3}$ | 0 | $2.33 \times 10^{-3}$ | 0 |
| 240db (mol/min) | $5.58 \times 10^{-5}$ | $5.58 \times 10^{-5}$ | 0 | 0 | 0 | 0 |
| 1234yf (mol/min) | 0 | 0 | $4.53 \times 10^{-5}$ | $4.53 \times 10^{-5}$ | 0 | 0 |
| 1233xf (mol/min) | 0 | $1.82 \times 10^{-4}$ | $1.82 \times 10^{-4}$ | 0 | $1.82 \times 10^{-4}$ | 0 |
| 245cb (mol/min) | 0 | $2.11 \times 10^{-5}$ | $2.11 \times 10^{-5}$ | 0 | $2.11 \times 10^{-5}$ | 0 |
| 1223xd (mol/min) | 0 | 0 | $3.39 \times 10^{-7}$ | 0 | 0 | $3.39 \times 10^{-7}$ |
| 1233zd (mol/min) | 0 | 0 | $3.02 \times 10^{-6}$ | 0 | 0 | $3.02 \times 10^{-6}$ |
| 1234ze (mol/min) | 0 | 0 | $4.63 \times 10^{-6}$ | 0 | 0 | $4.63 \times 10^{-6}$ |
| 245fa (mol/min) | 0 | 0 | 0 | 0 | 0 | 0 |
| 1243zf (mol/min) | 0 | 0 | 0 | 0 | 0 | 0 |
| Others (mol/min) | 0 | 0 | $2.50 \times 10^{-4}$ | 0 | 0 | $2.50 \times 10^{-4}$ |
| HCl (mol/min) | 0 | 0 | $2.79 \times 10^{-4}$ | $2.79 \times 10^{-4}$ | 0 | 0 |

Comparative Examples 1 to 3

With regard to Examples 1-2, 2, and 3 of Patent Document 4, a method of successively performing the operation by circulating the entire amount of HCFO-1233xf and HF in the components obtained from the reactor outlet to the reactor as disclosed in Patent Document 4 was considered. Table 4 shows the reaction conditions and the formulations of the reactor outlet in Examples 1-1 to 3 of Patent Document 4. As Comparative Examples 1 to 3, simulations were performed according to the flow shown in FIG. 1 in a manner such that the molar ratios $W/F_0$ and HF/240db were identical to those specified in the reaction conditions in Examples 1-2, 2, and 3 of Patent Document 4. The formulations of the components at each stage (F1 to F6 in FIG. 1) of the reaction step were analyzed using gas chromatography. Tables 5 to 7 show the results of Comparative Examples 1 to 3.

Table 8 shows the reaction conditions, the production amounts of HFO-1234yf, and the yields of HFO-1234yf relative to the supplied HCC-240db in Examples 1 and 2 and Comparative Examples 1 to 3.

As shown in Tables 5 to 7, the entire amount of HCFO-1233xf and HF in the components obtained from the reactor outlet cannot be circulated, and it was necessary to supply a part of them to a different process. This is evidently because the flow rates between the reactor inlet and the outlet were not balanced, and therefore it became necessary to supply unreacted HF or excessive HCFO-1233xf that can be used as intermediates of HFO-1234yf to a different process.

Further, as shown in Table 8, when the present invention is adopted, HFO-1234yf can be produced in an industrially advantageous manner in substantially a single reaction step.

TABLE 4

| | Example 1-1 | Example 1-2 | Example 2 | Example 3 |
|---|---|---|---|---|
| Reaction Temperature (° C.) | 360 | 360 | 355 | 345 |
| Molar Ratio (HF/240db) | 16 | 16 | 28 | 24 |
| W/F$_0$ (g · sec./cc) | 6.0 | 6.0 | 10.1 | 10.1 |
| O$_2$/240db (mol %) | 20 | 20 | 10 | 25 |
| Time Lapsed after Beginning of the Reaction Time (h) | 22 | 165 | 39 | 28 |
| Starting Material Conversion (%) | 100 | 100 | 100 | 100 |
| Selectivity of Useful Materials (%) | | | | |
| HFO-1234yf | 13.6 | 13.7 | 16.3 | 12.5 |
| HCFC-1233xf | 79.9 | 79.6 | 77.2 | 82.6 |
| HFC-245cb | 2.4 | 2.5 | 4.3 | 3.4 |
| Selectivity of Impurities (%) | | | | |
| HCFC-1223xd | 2.1 | 2.1 | 1.0 | 0.7 |
| HCFC-1233zd | 0.3 | 0.3 | 0.2 | 0.1 |
| HFO-1234ze | 0.2 | 0.2 | 0.1 | 0.1 |
| HFC-245fa | 0.1 | 0.1 | 0.1 | 0 |
| HFC-1243zf | 0.2 | 0.2 | 0.1 | 0.1 |
| Others | 1.2 | 1.3 | 0.7 | 0.5 |

TABLE 5

| Stage of the Step | F1 | F2 | F3 | F4 | F5 | F6 |
|---|---|---|---|---|---|---|
| HF (mol/min) | $1.40 \times 10^{-3}$ | $7.14 \times 10^{-3}$ | $5.74 \times 10^{-3}$ | 0 | $5.74 \times 10^{-3}$ | 0 |
| 240db (mol/min) | $4.46 \times 10^{-4}$ | $4.46 \times 10^{-4}$ | 0 | 0 | 0 | 0 |
| 1234yf (mol/min) | 0 | 0 | $6.07 \times 10^{-5}$ | $6.07 \times 10^{-5}$ | 0 | 0 |
| 1233xf (mol/min) | 0 | 0 | $3.57 \times 10^{-4}$ | 0 | 0 | $3.57 \times 10^{-4}$ |
| 245cb (mol/min) | 0 | 0 | $1.07 \times 10^{-5}$ | 0 | 0 | $1.07 \times 10^{-5}$ |
| 1223xd (mol/min) | 0 | 0 | $9.38 \times 10^{-6}$ | 0 | 0 | $9.38 \times 10^{-6}$ |
| 1233zd (mol/min) | 0 | 0 | $1.34 \times 10^{-6}$ | 0 | 0 | $1.34 \times 10^{-6}$ |
| 1234ze (mol/min) | 0 | 0 | $8.93 \times 10^{-7}$ | 0 | 0 | $8.93 \times 10^{-7}$ |
| 245fa (mol/min) | 0 | 0 | $4.46 \times 10^{-7}$ | 0 | 0 | $4.46 \times 10^{-7}$ |
| 1243zf (mol/min) | 0 | 0 | $8.93 \times 10^{-7}$ | 0 | 0 | $8.93 \times 10^{-7}$ |
| Others (mol/min) | 0 | 0 | $5.36 \times 10^{-6}$ | 0 | 0 | $5.36 \times 10^{-6}$ |
| HCl (mol/min) | 0 | 0 | $2.23 \times 10^{-3}$ | $2.23 \times 10^{-3}$ | 0 | 0 |

TABLE 6

| Stage of the Step | F1 | F2 | F3 | F4 | F5 | F6 |
|---|---|---|---|---|---|---|
| HF (mol/min) | $1.15 \times 10^{-3}$ | $1.00 \times 10^{-2}$ | $8.85 \times 10^{-3}$ | 0 | $8.85 \times 10^{-3}$ | 0 |
| 240db (mol/min) | $3.57 \times 10^{-4}$ | $3.57 \times 10^{-4}$ | 0 | 0 | 0 | 0 |
| 1234yf (mol/min) | 0 | 0 | $5.82 \times 10^{-5}$ | $5.82 \times 10^{-5}$ | 0 | 0 |
| 1233xf (mol/min) | 0 | 0 | $2.76 \times 10^{-4}$ | 0 | 0 | $2.76 \times 10^{-4}$ |
| 245cb (mol/min) | 0 | 0 | $1.54 \times 10^{-5}$ | 0 | 0 | $1.54 \times 10^{-5}$ |
| 1223xd (mol/min) | 0 | 0 | $3.57 \times 10^{-6}$ | 0 | 0 | $3.57 \times 10^{-6}$ |
| 1233zd (mol/min) | 0 | 0 | $7.14 \times 10^{-7}$ | 0 | 0 | $7.14 \times 10^{-7}$ |
| 1234ze (mol/min) | 0 | 0 | $3.57 \times 10^{-7}$ | 0 | 0 | $3.57 \times 10^{-7}$ |
| 245fa (mol/min) | 0 | 0 | $3.57 \times 10^{-7}$ | 0 | 0 | $3.57 \times 10^{-7}$ |
| 1243zf (mol/min) | 0 | 0 | $3.57 \times 10^{-7}$ | 0 | 0 | $3.57 \times 10^{-7}$ |
| Others (mol/min) | 0 | 0 | $2.50 \times 10^{-6}$ | 0 | 0 | $2.50 \times 10^{-6}$ |
| HCl (mol/min) | 0 | 0 | $1.79 \times 10^{-3}$ | $1.79 \times 10^{-3}$ | 0 | 0 |

TABLE 7

| Stage of the Step | F1 | F2 | F3 | F4 | F5 | F6 |
|---|---|---|---|---|---|---|
| HF (mol/min) | $1.13 \times 10^{-3}$ | $8.57 \times 10^{-3}$ | $7.44 \times 10^{-3}$ | 0 | $7.44 \times 10^{-3}$ | 0 |
| 240db (mol/min) | $3.57 \times 10^{-4}$ | $3.57 \times 10^{-4}$ | 0 | 0 | 0 | 0 |
| 1234yf (mol/min) | 0 | 0 | $4.46 \times 10^{-5}$ | $4.46 \times 10^{-5}$ | 0 | 0 |
| 1233xf (mol/min) | 0 | 0 | $2.95 \times 10^{-4}$ | 0 | 0 | $2.95 \times 10^{-4}$ |
| 245cb (mol/min) | 0 | 0 | $1.21 \times 10^{-5}$ | 0 | 0 | $1.21 \times 10^{-5}$ |
| 1223xd (mol/min) | 0 | 0 | $2.50 \times 10^{-6}$ | 0 | 0 | $2.50 \times 10^{-6}$ |
| 1233zd (mol/min) | 0 | 0 | $3.57 \times 10^{-7}$ | 0 | 0 | $3.57 \times 10^{-7}$ |
| 1234ze (mol/min) | 0 | 0 | $3.57 \times 10^{-7}$ | 0 | 0 | $3.57 \times 10^{-7}$ |
| 245fa (mol/min) | 0 | 0 | 0 | 0 | 0 | 0 |
| 1243zf (mol/min) | 0 | 0 | $3.57 \times 10^{-7}$ | 0 | 0 | $3.57 \times 10^{-7}$ |
| Others (mol/min) | 0 | 0 | $1.79 \times 10^{-6}$ | 0 | 0 | $1.79 \times 10^{-6}$ |
| HCl (mol/min) | 0 | 0 | $1.79 \times 10^{-3}$ | $1.79 \times 10^{-3}$ | 0 | 0 |

TABLE 8

| | Example 1 | Example 2 | Comparative Example 1 | Comparative Example 2 | Comparative Example 3 |
|---|---|---|---|---|---|
| Reaction Temperature (° C.) | 365 | 380 | 360 | 355 | 345 |
| $W/F_0$ (g · sec · ml$^{-1}$) | 10.4 | 14.3 | 6.0 | 10.1 | 10.1 |
| Reaction Pressure (MPaG) | 0.0 | 0.12 | 0.0 | 0.0 | 0.0 |
| Molar Ratio*[1] of HF/240db Supplied to the Reactor | 90.5 | 45.6 | 16 | 18 | 24 |
| HFO-1234yf Generation Amount (mol/g/min)*[2] | $2.25 \times 10^{-6}$ | $3.02 \times 10^{-6}$ | $3.57 \times 10^{-6}$ | $1.5 \times 10^{-6}$ | $1.3 \times 10^{-6}$ |
| Molar Ratio of 240db*[1] Supplied to the Reactor/HCFO-1233xf*[2] at the Outlet of the Reactor | 0.128 | 0.307 | 1.249 | 1.293 | 1.210 |
| HCl Concentration at the Outlet of the Reactor (mol %)*[2] | 9.2 | 6.8 | 26.7 | 16.3 | 18.8 |
| Yield of HFO-1234yf (%) | 87.2 | 81.2 | 13.6 | 16.3 | 12.5 |

*[1]value at F2
*[2]value at F3

The invention claimed is:

1. A method for producing 2,3,3,3-tetrafluoropropene (HFO-1234yf), comprising a reaction step of reacting at least one chlorine-containing starting compound selected from the group consisting of:
chlorine-containing alkanes of the following formula (1):

wherein X, Y and Z independently represent H, F or Cl; and
chlorine-containing alkenes of the following formula (2):

wherein X, Y and Z independently represent H, F or Cl, with a fluorinating agent in a reactor at a pressure of 0 to 0.3 MPaG,
wherein a concentration of HCl contained in components obtained from a reactor outlet in the reaction step is 10 mol % or less relative to a total amount of the components obtained from the reactor outlet.

2. The method according to claim 1, wherein a molar ratio of the fluorinating agent supplied to the reactor is more than 50 relative to a molar amount of the chlorine-containing starting compound newly supplied to a reactor inlet.

3. The method according to claim 1, wherein a molar ratio of the chlorine-containing starting compound newly supplied to a reactor inlet is 0.3 or less relative to a molar amount of HCFO-1233xf in the components obtained from the reactor outlet.

4. The method according to claim 1, further comprising circulating at least a part of a product of the reaction step, and unreacted chlorine-containing starting compound and fluorinating agent in the reactor outlet to the reaction step.

5. The method according to claim 1, further comprising separating HFO-1234yf and/or HCl from a product of the reaction step obtained in the reactor outlet, and circulating at least a part of a remaining product, and unreacted chlorine-containing starting compound and fluorinating agent to the reaction step.

6. The method according to claim 1, wherein at least one chlorine-containing starting compound of the compounds of formula (1) is 1,1,1,2,3-pentachloropropane (HCC-240 db).

7. The method according to claim 1, wherein at least one chlorine-containing starting compound of the compounds of formula (2) is 1,1,2,3-tetrachloropropene (HCO-1230xa).

8. The method according to claim 1, wherein the fluorinating agent is anhydrous hydrogen fluoride.

9. The method according to claim 1, wherein a catalyst used in the reaction step is a chromium oxide or a fluorinated chromium oxide.

10. The method according to claim 1, wherein a concentration of HCl contained in components that are circulated to the reaction step is 5 mol % or less relative to a chlorine-containing compound to be circulated.

11. The method according to claim 1, wherein $O_2$ and/or $Cl_2$ is introduced in the reaction step.

\* \* \* \* \*